(12) United States Patent
Geiser et al.

(10) Patent No.: US 10,561,314 B2
(45) Date of Patent: Feb. 18, 2020

(54) DEVICE FOR MEASURING THE SPEED OF BLOOD IN A BLOOD VESSEL OF THE EYE

(71) Applicant: UNIVERSITE GRENOBLE ALPES, Saint Martin d'Heres (FR)

(72) Inventors: Martial Henri Geiser, Sion (CH); Frédéric Truffer, Randa (CH); Helene Strese, Peckelsheim (DE); Christophe Chiquet, Montbonnot Saint Martin (FR)

(73) Assignee: UNIVERSITE GRENOBLE ALPES, Saint Martin d'Heres (FR)

( * ) Notice: Subject to any disclaimer, the term of this patent is extended or adjusted under 35 U.S.C. 154(b) by 15 days.

(21) Appl. No.: 15/767,566

(22) PCT Filed: Oct. 28, 2016

(86) PCT No.: PCT/FR2016/052818
§ 371 (c)(1),
(2) Date: Apr. 11, 2018

(87) PCT Pub. No.: WO2017/072468
PCT Pub. Date: Apr. 5, 2017

(65) Prior Publication Data
US 2018/0303338 A1 Oct. 25, 2018

(30) Foreign Application Priority Data
Oct. 30, 2015 (FR) ..................................... 15 60450

(51) Int. Cl.
*A61B 3/12* (2006.01)
*A61B 3/15* (2006.01)
(Continued)

(52) U.S. Cl.
CPC ............ *A61B 3/1233* (2013.01); *A61B 3/154* (2013.01); *A61B 3/1025* (2013.01); *G01P 5/26* (2013.01); *G01S 17/58* (2013.01)

(58) Field of Classification Search
CPC ........... A61B 3/0008; A61B 3/14; A61B 3/12; A61B 3/102; A61B 3/0025
(Continued)

(56) References Cited

U.S. PATENT DOCUMENTS

| 5,900,928 A * | 5/1999 | Riva .................... A61B 3/1025 356/28.5 |
| 2005/0254008 A1* | 11/2005 | Ferguson ............. A61B 3/1025 351/205 |
| 2015/0092195 A1 | 4/2015 | Blatter et al. |

FOREIGN PATENT DOCUMENTS

CN 1376445 A 10/2002

OTHER PUBLICATIONS

Officer Giovanni Tommaseo, "International Search Report and the Written Opinion", International Patent Application PCT/FR2016/052818, dated Feb. 1, 2017, 14 pp.

* cited by examiner

*Primary Examiner* — Mohammed A Hasan
(74) *Attorney, Agent, or Firm* — Kaplan Breyer Schwarz, LLP

(57) ABSTRACT

The invention relates to a device for measuring the speed of blood in a blood vessel of the eye. Said device includes: a light source (5), two detectors provided with input diaphragms (36, 46) for receiving two light beams backscattered by a blood vessel, an optical system including a Dove prism (70) through which the source beam and backscattered beams pass and which is rotatably adjustable about an axis parallel to the source beam passing therethrough, and a focusing system (62) capable of forming the image of a blood vessel on the input diaphragms, a processor capable of processing the signals from the detectors, and an opitcal element (52) that can be inserted during the device adjustment phase so as to convert the light spot, provided by the
(Continued)

light source, into a line coplanar with the source beam and the backscattered beams.

3 Claims, 4 Drawing Sheets

(51) Int. Cl.
 *A61B 3/10* (2006.01)
 *G01P 5/26* (2006.01)
 *G01S 17/58* (2006.01)
(58) Field of Classification Search
 USPC .......................................................... 351/221
 See application file for complete search history.

DEVICE FOR MEASURING THE SPEED OF BLOOD IN A BLOOD VESSEL OF THE EYE

The present patent application claims the priority benefit of French patent application FR15/60450 which is herein incorporated by reference.

BACKGROUND

The present application concerns a device for measuring the speed of blood in a blood vessel of the eye. Such a device is currently called laser Doppler velocimeter and designated with acronym LDV.

DISCUSSION OF THE RELATED ART

A laser Doppler velocimeter is described in U.S. Pat. No. 5,900,928, having, as one of its inventors, one of the inventors of the present application.

The accompanying FIG. 1 is a copy of FIG. 2 of U.S. Pat. No. 5,900,928, the reference numerals having been modified. A laser 1 sends through an aperture 3 a light beam 5 towards an optical system 7, which sends beam 5 towards an eye 10 and more particularly towards a blood vessel 12 of the fundus of this eye. The vessel backscatters light. Optical system 7 re-addresses, via a mirror 16, beams 14 and 15 of the backscattered light towards an entrance aperture 17 of a detection system 20, which particularly enables to determine the speed of the blood flow in the blood vessel. Optical system 7 is capable of providing confocal connections between the different planes of the system.

The device described in U.S. Pat. No. 5,900,928 operates satisfactorily but is very difficult to adjust, particularly due to the confocal coupling of the various entrance and exit pupils.

SUMMARY

Thus, an object of the invention is to provide a system ensuring the same laser Doppler velocimetry functions as those described in U.S. Pat. No. 5,900,928 but which is simpler to form and to adjust.

An embodiment provides a device for measuring the speed of blood in a blood vessel of the eye, comprising: a coherent light source for generating a source beam; two detectors provided with entrance apertures for receiving two light beams backscattered by a blood vessel; an optical system comprising a Dove prism crossed by the source beam and the backscattered beams and capable of being rotatably adjusted around an axis parallel to the source beam crossing it, and a focusing system capable of forming the image of a blood vessel on the entrance apertures; a signal processor capable of processing the signals from the detectors; and an optical element which can be inserted during the device adjustment phase to transform the light spot supplied by the light source into a line coplanar with the source beam and the backscattered beams selected by the apertures, the device being coupled with a fundus camera to aim into the fundus of the eye at a selected blood vessel and to align said line with the tangent to the blood vessel at the illumination point by means of a rotation of the Dove prism.

According to an embodiment, the light source is an infrared laser.

According to an embodiment, the optical element for transforming a light spot into a line is a grating or a cylindrical lens.

BRIEF DESCRIPTION OF THE DRAWINGS

The foregoing and other features and advantages will be discussed in detail in the following non-limiting description of specific embodiments in connection with the accompanying drawings, in which.

For clarity, the same elements have been designated with the same reference numerals in the different drawings.

DETAILED DESCRIPTION

Figure 1:
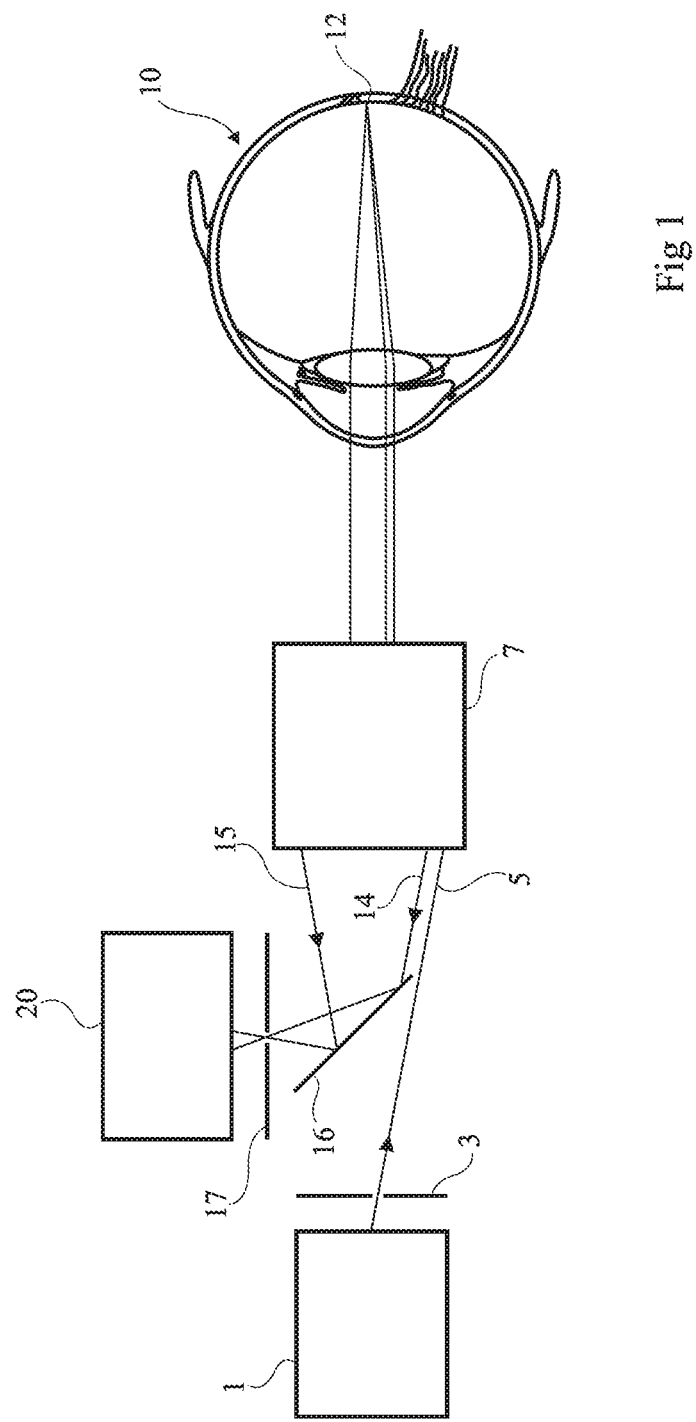
FIG. 1, previously described, shows a laser Doppler velocimeter.
Figure 2:
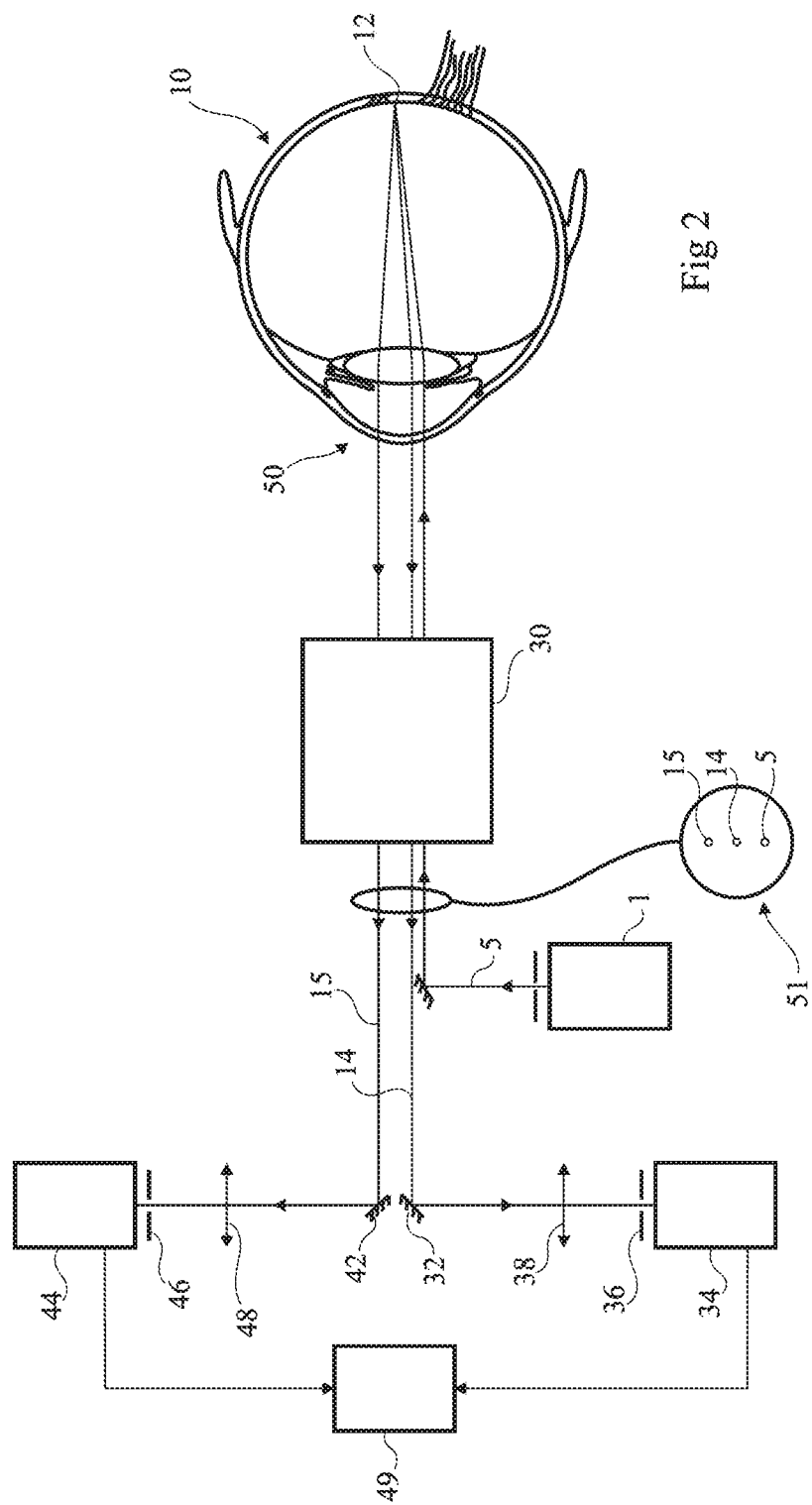
FIG. 2 is a schematic diagram of an embodiment of a laser Doppler velocimeter.

As shown in FIG. 2, an embodiment of a velocimeter intended for the analysis of a blood vessel 12 of an eye 10 comprises a laser source 1 intended to emit a light beam 5 towards the fundus of eye 10. The laser beam runs through an optical system 30. The light backscattered by blood vessel 12 crosses optical system 30 again. A beam 14 of the backscattered light is reflected by a mirror 32 towards a detector 34 preceded by an aperture 36 and by a focusing lens 38. Another beam 15 of the backscattered light is reflected by a mirror 42 towards a detector 44 preceded by an aperture 46 and by a focusing lens 48. Detectors 34 and 44 are coupled to a signal processor 49.

A first function of optical system 30 is to conjugate the openings of apertures 36 and 46 with blood vessel 12. Cross-section 51 shows the points of impact of the transmitted beam 5 and of return beams 14 and 15 in a plane perpendicular to the plane of the drawing. This cross-section shows that optical system 30 is configured and that apertures 36 and 46 are arranged so that optical beams 14 and 15 received by the detectors and beam 5 emitted by the laser are conjugated to define a plane.

Optical system 30 has a second function, which is to allow a rotation of the plane of the emitted beam and of the received beams in the plane of pupil 50. This function is for example ensured by a Dove prism. One may accordingly, as described in further detail in relation with FIG. 3, rotate the plane defined hereabove around the optical axis of the system so that the plane contains the tangent to the blood vessel at the point of impact of the laser beam on the vessel.

Then, the detection of the two backscattered light beams in different directions with a known angle between these directions enables to calculate the blood speed in the blood vessel even though the exact angle of incidence of the laser beam is not known. The plane defined hereabove should further contain the tangent to the blood vessel at the illumination point thereof.

Figure 3:
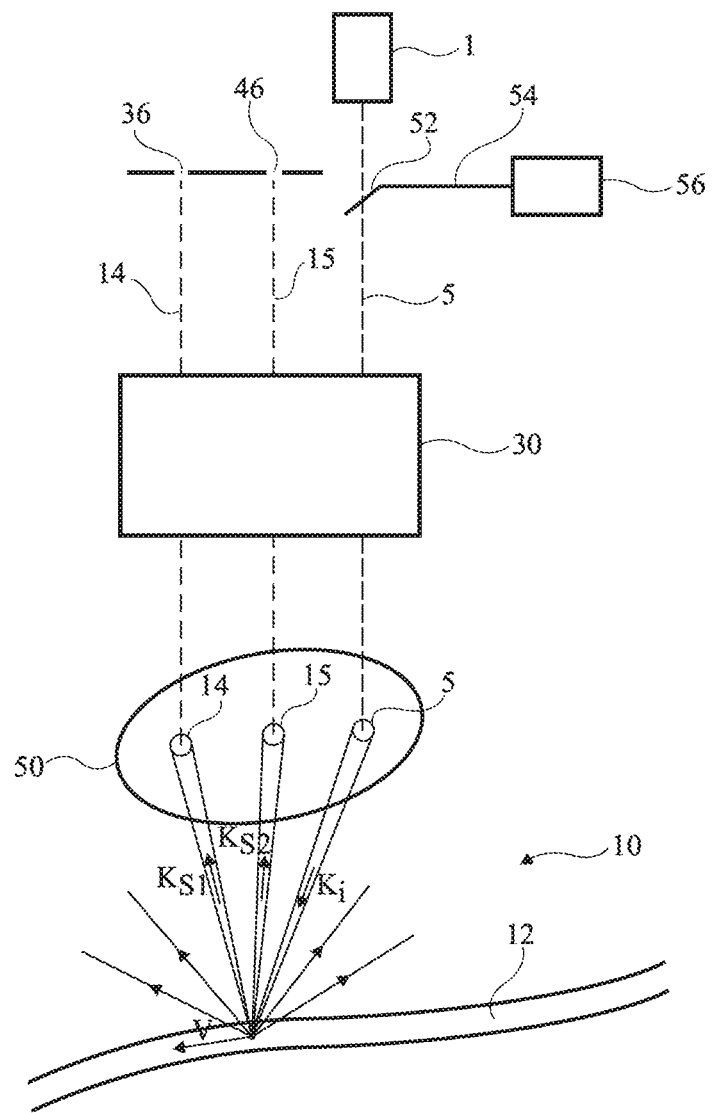
FIG. 3 shows a detail of the velocimeter of FIG. 2.

FIG. 3 shows a portion of the previously-described device. One can see, at the top of the drawing, laser 1 emitting beam 5, aperture 36 receiving light beam 14, and aperture 46 receiving light beam 15. Beam 5 runs through optical system 30 and reaches the level of input pupil 50 of eye 10. Beam 5 is directed according to a vector Ki towards a point of a blood vessel 12 having beams, from which beams 14 and 15 are sampled, backscattered therefrom. The system is arranged as previously indicated so that director vectors $K_{S1}$ and $K_{S2}$ of beams 14 and 15 are coplanar with the incident vector Ki.

On the other hand, as previously indicated, it is desired for the vector tangent to the blood vessel at the location of the impact (collinear with speed vector V of the blood in the blood vessel) to also be coplanar with vectors Ki, $K_{S1}$, and $K_{S2}$. The rotation of the Dove prism comprised in optical system 30 enables to ensure such a coplanarity.

However, a problem is posed to experimentally verify that the four vectors V, Ki, $K_{S1}$, and $K_{S2}$ are effectively coplanar.

To be sure of the coplanarity, a removable optical element 52 is used, for example, an optical grating or a cylindrical lens, assembled at the end of a swivel arm 54 coupled to frame 56 of the device. Such a grating or cylindrical lens is selected and oriented so that the circular spot of the laser beam is transformed into a line, the line extending in the plane of beam 5 and of the beams 14 and 15 received by the apertures. Thus, at the level of the fundus of the eye, the impact of beam 5 becomes a line located in the plane of vectors Ki, $K_{S1}$, and $K_{S2}$. The trace of this line may be simultaneously observed by a fundus camera (a device currently used by opticians and ophthalmologists) or directly observed by an observer. The Dove prism may thus be angularly adjusted so that the four vectors V, Ki, $K_{S1}$, and $K_{S2}$ are effectively coplanar. If laser 1 emits, as is the current case, a beam in the infrared range, a camera sensitive to infrared will be used.

Of course, the present invention is likely to have many variations conventional in optics and particularly, for example, for the sake of compactness, various reflection mirrors ensuring the folding of beams may be provided.

Figure 4:
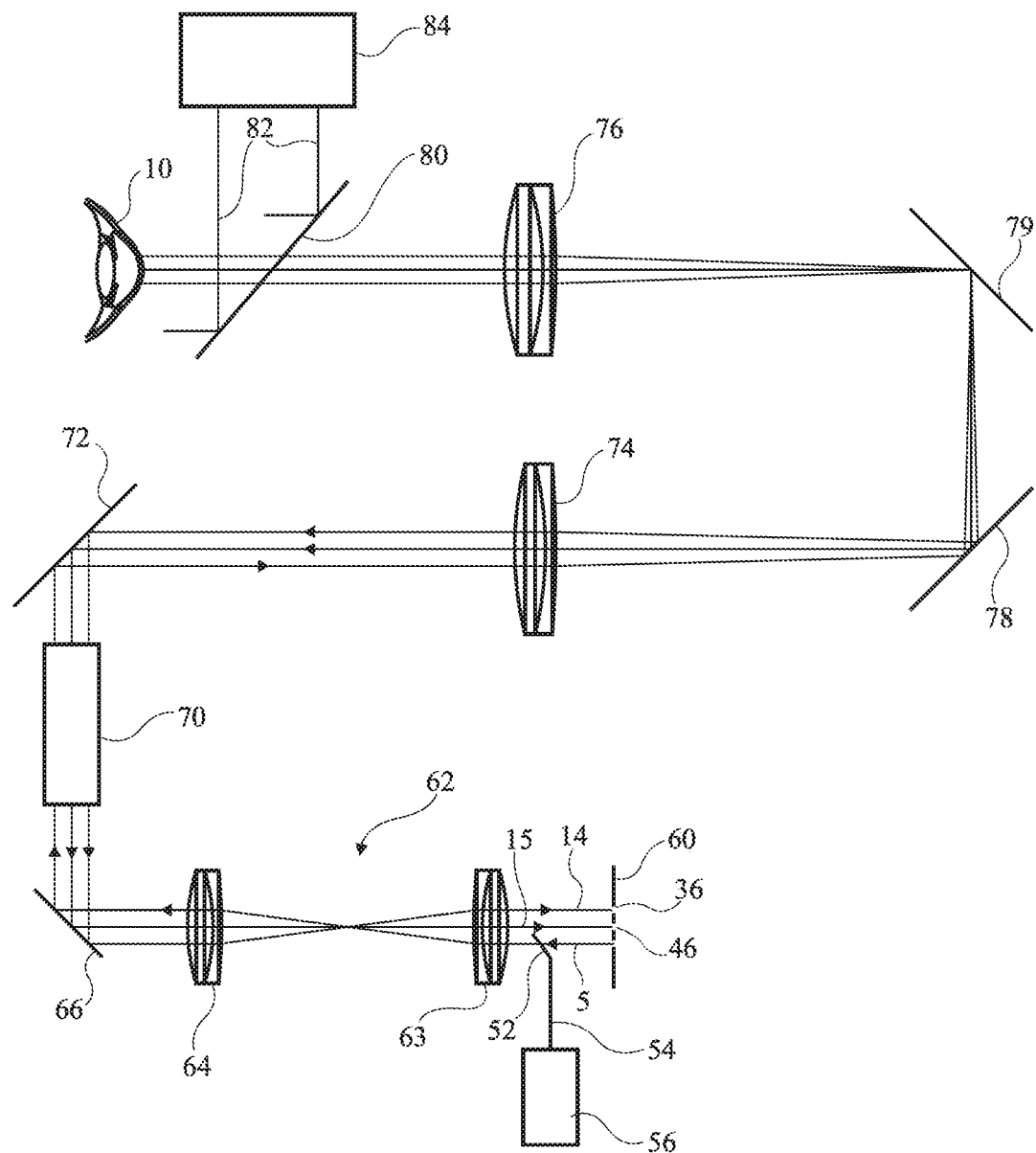
FIG. 4 shows an embodiment of the velocimeter of FIG. 2.

A specific embodiment is illustrated in FIG. 4, where an entrance aperture plate 60 comprises above-mentioned apertures 36 and 46 as well as an aperture to let through laser beam 5. An objective 62 comprises lenses 63 and 64. The output of this objective is sent via a folding mirror 66 to a Dove prism 70. The beam coming out of Dove prism 70 may be directly sent to the eye to be analyzed. In the shown embodiment, the beam is folded by a mirror 72 towards an optical system with a magnification smaller than 1, comprising two lenses 74 and 76 ensuring the transmission of the various beams to eye 10. The beam-folding mirrors 78 and 79 are provided between lenses 74 and 76. A device having a compact structure is thus obtained. Further, although this has not been shown, means of rotation around its axis are coupled to Dove prism 70 to adjust the coplanarity of the four vectors V, Ki, $K_{S1}$, and $K_{S2}$ as mentioned in relation with FIG. 3.

FIG. 4 also shows removable arm 54 coupled to frame 56 and supporting optical element 52 enabling, during the device adjustment phase, to transform as indicated the light spot supplied by laser beam 5 into a line.

FIG. 4 also shows, as an example, a beam splitter 80 enabling to direct the incoming and exiting beams 82 of a fundus camera 84 towards the fundus of the eye. Camera 84 enables to verify the positioning of the laser spot on a selected blood vessel. It also enables, during an adjustment phase, to properly orient by means of the Dove prism the line provided by optical element 52 (for example, a grating or a cylindrical lens) towards the targeted blood vessel. As noted, instead of using a camera, an observer may directly observe the fundus of the eye via the beam splitter.

The invention claimed is:

1. A device for measuring the speed of blood in a blood vessel of the eye, comprising:
    a coherent light source for generating a source beam;
    two detectors provided with entrance apertures to receive two light beams backscattered by a blood vessel;
    an optical system comprising;
        a Dove prism crossed by the source beam and the backscattered beams and capable of being rotatably adjusted around an axis parallel to the source beam crossing it, and
        a focusing system capable of forming the image of a blood vessel on the entrance apertures;
    a signal processor capable of processing the signals from the detectors; and
    a removable optical element which is inserted only during the device adjustment phase to transform the light spot supplied by the light source into a line coplanar with the source beam and the backscattered beams selected by the apertures,
    the device being coupled with a fundus camera to aim into the fundus of the eye at a selected blood vessel and to align said line with the tangent to the blood vessel at the illumination point by means of a rotation of the Dove prism.

2. The measurement device of claim 1, wherein the light source is an infrared laser.

3. The device of claim 1, wherein the removable optical element for transforming a light spot into a line is a grating or a cylindrical lens.

* * * * *